United States Patent [19]

Franke et al.

[11] 4,060,733

[45] Nov. 29, 1977

[54] X-RAY DIAGNOSTIC APPARATUS WITH AN AUTOMATIC EXPOSURE TIMER

[75] Inventor: Kurt Franke, Erlangen, Germany

[73] Assignee: Siemens Aktiengesellschaft, Berlin & Munich, Germany

[21] Appl. No.: 623,071

[22] Filed: Oct. 16, 1975

[30] Foreign Application Priority Data

Oct. 18, 1974 Germany .............................. 2449708

[51] Int. Cl.² ............................................ G01N 23/02
[52] U.S. Cl. .................................................. 250/491
[58] Field of Search ................ 250/491, 322, 476, 505

[56] References Cited

U.S. PATENT DOCUMENTS

| 2,455,928 | 12/1948 | Hawks | 250/491 |
| 2,623,180 | 12/1952 | Zurli et al. | 250/491 |
| 2,955,205 | 10/1960 | Camfferman | 250/491 |
| 3,679,902 | 7/1972 | Hurst et al. | 250/476 |

Primary Examiner—Alfred E. Smith
Assistant Examiner—B. C. Anderson

Attorney, Agent, or Firm—Hill, Gross, Simpson, Van Santen, Steadman, Chiara & Simpson

[57] ABSTRACT

An X-ray diagnostic installation which includes an automatic exposure timer. An X-ray diagnostic installation of the above type is so constructed whereby the setting or positioning of the measuring probe is substantially simplified in contrast with the state of the technology. Located in the housing of the primary ray focusing diaphragm, is an adjustable marking installation which is optically reproducible on the patient, for the imaging or reproduction of a measuring area, and in which there is located on the exterior of the shutter housing at least one scale for reading off its positioning, and wherein the measuring probe is connected with setting means which project out of the cassette drawer, having associated therewith at least one scale for reading off the position of the measuring probe. The user may, in the inventive X-ray diagnostic installation, read off the coordinates of the selected measuring area on the diaphragm housing of the X-ray generator and utilize these coordinates for the setting or positioning of the measuring probe.

4 Claims, 5 Drawing Figures

X-RAY DIAGNOSTIC APPARATUS WITH AN AUTOMATIC EXPOSURE TIMER

FIELD OF THE INVENTION

The present invention relates to an X-ray diagnostic installation which includes an automatic exposure timer.

DISCUSSION OF THE PRIOR ART

An X-ray diagnostic installation is currently known which is constituted of a portable X-ray generator and a cassette drawer within which an X-ray film cassette is insertable, and which is placed below the patient. As viewed in the ray direction, in back of the X-ray film there is located the measuring probe of an automatic exposure timer in this cassette drawer. This measuring probe may be positioned in conformance with the desired measuring area. The X-ray generator contains a light visor which facilitates the X-radiation to be so focused whereby only the X-ray film is struck by X-radiation.

In the known X-ray diagnostic installation it is disadvantageous in that the positioning of the measuring probe is difficult inasmuch as its location is not ascertainable from the exterior and, consequently, cannot be adjusted from exteriorly in conformance with the desired measuring area. The positioning of the measuring probe in the known X-ray diagnostic installation is carried out with an opened cassette drawer. The measuring probe is thereby maintained in its present position by means of an adhesive magnet.

SUMMARY OF THE INVENTION

Accordingly, it is an object of the present invention to provide an X-ray diagnostic installation of the above type which is so constructed whereby the setting or positioning of the measuring probe is substantially simplified in contrast with the state of the technology.

The foregoing object is inventively attained in that, located in the housing of the primary ray focusing diaphragm, is an adjustable marking installation which is optically reproducible on the patient for the imaging or reproduction of a measuring area, and in which there is located on the exterior of the shutter housing at least one scale for reading off its positioning, and wherein the measuring probe is connected with setting means which project out of the cassette drawer, having associated therewith at least one scale for reading off the position of the measuring probe. The user may, in the inventive X-ray diagnostic installation, read off the coordinates of the selected measuring area on the diaphragm housing of the X-ray generator and utilize these coordinates for the setting or positioning of the measuring probe.

BRIEF DESCRIPTION OF THE DRAWINGS

Further advantages and details of the invention may now be ascertained from the following description of an exemplary embodiment thereof, taken in conjunction with the accompanying drawings; in which.

DETAILED DESCRIPTION

Figure 1:
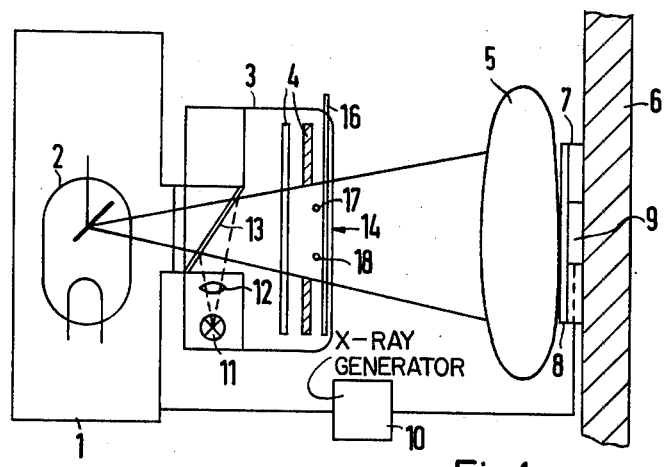
FIG. 1 is a schematic representation of an X-ray diagnostic installation which is constructed pursuant to the invention.

In FIG. 1 there is illustrated a housing within which there is located an X-ray tube 2. The X-radiation passes through a shutter or diaphragm housing 3 in which there is located a primary X-ray focusing diaphragm which facilitates the focusing of a rectangularly-shaped area. Of the primary X-ray focusing diaphragm, visible are the aperture plates 4. The X-radiation passes through a patient 5 who is lying on a patient support pallet 6. Arranged between the patient 5 and the support pallet 6 is a cassette drawer 7, in which there is located an X-ray film cassette 8. The cassette drawer 7 further contains the measuring probe 9 of an automatic exposure timer which is a component of an X-ray generator 10 supplying the X-ray tube 2.

The measuring probe 9 detects the ray dosage and, together with the automatic exposure timer, effects the switching off of the X-ray tube 2 pursuant to a predetermined dosage corresponding to an optimum film darkening. An X-ray apparatus which includes an automatic exposure timer is described, for example, in U.S. Pat. No. 2,929,000.

Figure 2:
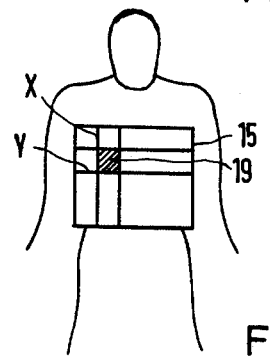
FIG. 2 shows a plan view of a patient with a setting image which is producible by means of the X-ray diagnostic installation according to FIG. 1.

A light source 11 is located in the diaphragm housing 3, which beams on the patient 5, by means of an optical system 12 and a mirror 13, through the outlet aperture 14 of the diaphragm housing 3. The reproduced rectangularly-shaped area 15 according to FIG. 2 is hereby identical with the ray area which has been focused during the preparation of an X-ray tube, and may be correlated with the cassette 8 by means of the primary ray focusing diaphragm 4. The light visor which is constituted of components 11 through 13, in a known manner, thus facilitates an exact setting of the primary ray focusing diaphragm.

Figure 1A:
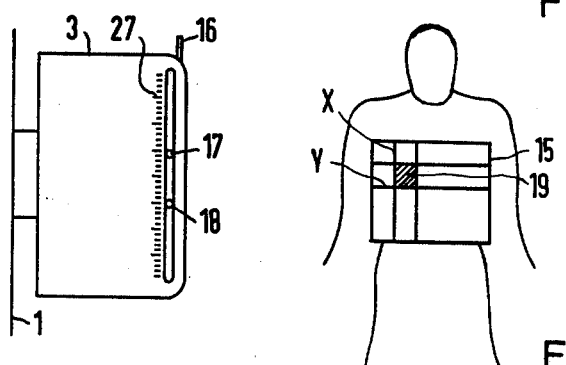
FIG. 1a shows a detail of the installation of FIG. 1.

In proximity to the X-ray outlet aperture 14 there are located four plastic material rods or shadow producing means, of which rods 16, 17 and 18 are visible in FIG. 1. These plastic material rods, pursuant to FIG. 2, are visible in the area reproduced by the light visor. They project outwardly from the diaphragm housing 3 and are manually adjustable in two mutually perpendicular directions, and namely, in parallel with respectively each two sides of the field or area reproduced by the light visor on the patient. It is thus possible to focus a rectangular area 19 by means of the rods 16 through 18 which are located at right angles to each other, behind which there is to be positioned the measuring probe 9, meaning an area within which there is to be attained an optimum degree of film darkening. The present position of the rods 16 through 18 is readable on a scale located on the diaphragm housing 3. Thus, for example, it is possible to read off the value $x$ and the value $y$. The scale is visible from the outside on the diaphragm housing 3 shown in elevation in FIG. 1a, and is designated by reference numeral 27.

Figure 3:
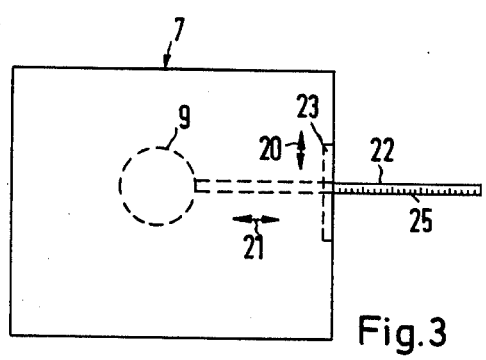
FIGS. 3 and 4, respectively, are plan and side elevational views of a cassette drawer in the X-ray diagnostic installation according to FIG. 1.
Figure 4:
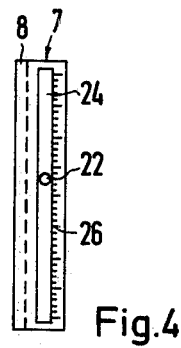

The measuring probe is displaceable within the cassette drawer 7, according to FIGS. 3 and 4, in the direction of the double-headed arrows 20 and 21 in parallel with the film plane. For this purpose, the measuring probe 9 is fastened to a rod 22 projecting outwardly from a slot 24 in perpendicular with a narrower side of the cassette drawer, and supported in a support piece 23 so as to be adjustable in the direction of the double-headed arrow 21. The support piece 21 further is adjustably supported along the narrower side of the cassette drawer along the longitudinal direction of this narrower side. The measuring probe 9 is thereby adjustable along the longitudinal direction of the rod and in perpendicular thereto. The rod 22, pursuant to FIG. 3, carries an X scale, and at the side of the slot 24, in which the rod 22 is displaceable in the direction of the double-headed arrow 20, there is located a scale 26. Should the measuring probe 9 be positioned in correspondence with the coordinates x and y, as shown in FIG. 2, then for a pregiven focus-film distance these coordinates are read off on the diaphragm housing 3, and the measuring probe 9 so adjusted that the x and y values which are read off on the scales 25 and 26 coincide with the x and y values which are read off on the diaphragm housing 3. At a focus-film distance which is drastically varied in contrast with the normal value, a correction may be assumed pursuant to a table.

From the drawing there may be ascertained that an exact positioning of the measuring probe 9 is possible in a simple manner, in that the values which are read off on the diaphragm housing 3 may be carried over to the measuring probe 9. For the reading off of these values, similar to what is illustrated in FIG. 1, the outwardly projecting ends of rods 16, 17 and 18 may be guided in slots in the diaphragm housing, at whose edge there are located scales.

While there has been shown what is considered to be the preferred embodiment of the invention, it will be obvious that modifications may be made which come within the scope of the disclosure of the specification.

What is claimed is:

1. An X-ray diagnostic installation comprising an X-ray tube housing having an X-ray tube mounted therewithin, an X-ray film cassette drawer disposed in spaced relation to said X-ray tube housing for receiving and holding a planar X-ray film cassette, a diaphragm housing disposed between said X-ray tube housing and said film cassette drawer and containing a primary X-ray focusing diaphragm and a light visor for illuminating a region of the body of a patient overlying said cassette drawer, an X-ray generator comprising an automatic X-ray exposure timer having a measuring probe adjustably positionable within said cassette drawer in parallel relation to the plane of the X-ray film cassette received therewithin, means operatively interconnecting said X-ray tube and said X-ray generator, said X-ray tube housing, said cassette drawer and said diaphragm housing being arranged in aligned relation with one another, shadow producing means adjustably positionable on said diaphragm housing in operative association with said light visor for producing an optically visual measuring area of selectively adjustable size and location on the body of the patient overlying said cassette drawer, first position determining means on said diaphragm housing for determining the position of said shadow producing means relative to said diaphragm housing, and second position determining means on said cassette drawer and on said measuring probe corresponding to said first position determining means for determining the position of said measuring probe relative to said cassette drawer and for positioning said measuring probe in alignment with the measuring area produced by said shadow producing means.

2. The invention as defined in claim 1 wherein said shadow producing means comprises a pair of elongated rods disposed at right angles with respect to one another projecting out beyond said diaphragm housing.

3. The invention as defined in claim 1 wherein said shadow producing means comprises two pairs of elongated rods projecting out beyond said diaphragm housing, said pairs of rods being arranged at right angles to one another and the rods of each pair being movable with respect to one another to produce a rectangular measuring area.

4. The invention as defined in claim 1 wherein said first and second position determining means comprise means forming scales on said diaphragm housing and on said cassette drawer respectively.

* * * * *